(12) United States Patent
Jennings

(10) Patent No.: US 10,533,956 B2
(45) Date of Patent: Jan. 14, 2020

(54) MULTI-DEPTH SOIL MOISTURE MONITORING SYSTEMS AND METHODS TO EVALUATE SOIL TYPE, PACKAGED IN SMALL ROUND POLYVINYL CHLORIDE TUBE, WITH POTTING AND RODENT PROTECTION, FOR EFFECTIVE MEASUREMENTS AND INSTALLATION

(71) Applicant: FarmX Inc., Redwood City, CA (US)

(72) Inventor: William E. Jennings, San Jose, CA (US)

(73) Assignee: FarmX Inc., Mountain View, CA (US)

( * ) Notice: Subject to any disclaimer, the term of this patent is extended or adjusted under 35 U.S.C. 154(b) by 37 days.

(21) Appl. No.: 15/836,748

(22) Filed: Dec. 8, 2017

(65) Prior Publication Data

US 2018/0164230 A1 Jun. 14, 2018

Related U.S. Application Data

(60) Provisional application No. 62/434,340, filed on Dec. 14, 2016.

(51) Int. Cl.
*G01N 22/04* (2006.01)
*G01N 33/24* (2006.01)

(52) U.S. Cl.
CPC .......... *G01N 22/04* (2013.01); *G01N 33/246* (2013.01)

(58) Field of Classification Search
CPC ....... G01N 22/04; G01N 33/24; G01N 33/246
(Continued)

(56) References Cited

U.S. PATENT DOCUMENTS

RE31,023 E    9/1982  Hall, III
4,590,477 A * 5/1986  Regnier ................ G01S 13/785
                                                        342/173
(Continued)

FOREIGN PATENT DOCUMENTS

WO    WO2016110832 A1    7/2016
WO    WO2018085452 A1    5/2018

OTHER PUBLICATIONS

EnviroSCAN Probe, [retrieved on Dec. 14, 2016], Retrieved from the Internet: <URL:http://www.sentek.com.au/products/enviro-scan-probe.asp>, 3 pages.

(Continued)

*Primary Examiner* — Giovanni Astacio-Oquendo
(74) *Attorney, Agent, or Firm* — Carr & Ferrell LLP

(57) ABSTRACT

According to some exemplary embodiments, the present disclosure is related in general to a soil moisture monitoring system comprising a first PVC pipe holding one or more sensing units, a top of the first PVC pipe mated to a "T" intersection, and a base of the "T" intersection mated to a rodent resistant cord. The first PVC pipe is generally round in shape with one or more flat surfaces of approximately six inches in length, each flat surface at an approximately 90 degree angle relative to a next closest flat surface. Each of the one or more sensing units further comprises a controller communicatively coupled between two antennas. In most exemplary embodiments, four sensing units may be vertically stacked on the first PVC pipe and configured to transmit eight separate directional radio frequencies into nearby dirt, each of the eight separate directional radio frequencies vertically spaced six inches apart.

20 Claims, 6 Drawing Sheets

(58) Field of Classification Search
USPC .................................. 324/600, 629, 637
See application file for complete search history.

(56) References Cited

U.S. PATENT DOCUMENTS

| | | | |
|---|---|---|---|
| 5,418,466 A | 5/1995 | Watson et al. | |
| 5,445,178 A | 8/1995 | Feuer | |
| 6,014,029 A | 1/2000 | Soto et al. | |
| 6,720,908 B1* | 4/2004 | Puglia | G01S 13/44 342/113 |
| 6,977,351 B1 | 12/2005 | Woytowitz | |
| 7,836,910 B2 | 11/2010 | Dresselhaus et al. | |
| 8,682,494 B1 | 3/2014 | Magro et al. | |
| 2002/0170229 A1 | 11/2002 | Ton et al. | |
| 2006/0057997 A1* | 3/2006 | Hausdorf | G01R 19/04 455/264 |
| 2006/0144437 A1 | 7/2006 | Dresselhaus et al. | |
| 2009/0326723 A1 | 12/2009 | Moore et al. | |
| 2010/0257633 A1 | 10/2010 | Pogson et al. | |
| 2012/0084115 A1 | 4/2012 | Cline et al. | |
| 2013/0341420 A1 | 12/2013 | Lister et al. | |
| 2014/0088770 A1 | 3/2014 | Masters et al. | |
| 2014/0326801 A1 | 11/2014 | Upadhyaya et al. | |
| 2015/0081058 A1 | 3/2015 | Oliver et al. | |
| 2015/0247787 A1* | 9/2015 | Yeomans | G01N 5/04 73/865 |
| 2015/0268218 A1* | 9/2015 | Troxler | G01S 13/0209 342/21 |
| 2015/0278719 A1 | 10/2015 | Schueller et al. | |
| 2015/0301536 A1 | 10/2015 | Martinez | |
| 2016/0037709 A1 | 2/2016 | Sauder et al. | |
| 2016/0135389 A1 | 5/2016 | Ersavas et al. | |
| 2016/0202227 A1 | 7/2016 | Mathur et al. | |
| 2017/0172077 A1 | 6/2017 | Wouhaybi et al. | |
| 2017/0311559 A1 | 11/2017 | Ebert et al. | |
| 2018/0080861 A1* | 3/2018 | Lafian | G01L 1/005 |
| 2018/0129175 A1 | 5/2018 | Jennings et al. | |
| 2018/0146631 A1 | 5/2018 | Haran et al. | |
| 2018/0146632 A1 | 5/2018 | Meron | |
| 2018/0164762 A1 | 6/2018 | Mewes et al. | |
| 2018/0202988 A1 | 7/2018 | Jennings | |
| 2018/0252694 A1 | 9/2018 | Mase et al. | |
| 2018/0259496 A1 | 9/2018 | McPeek | |

OTHER PUBLICATIONS

Liquid Sensing at Radio Frequencies, Complex impedance measurement of liquid samples as a function of frequency, [retrieved on Jan. 13, 2017] Microwave Journal, Thomas J. Warnagiris, Sep. 1, 2000, (http://www.microwavejournal.com/articles/3038-liquid-sensing-at-radio-frequencies), 9 pages.

"International Search Report" and "Written Opinion of the International Searching Authority", Patent Cooperation Treaty Application No. PCT/US2017/059597, dated Jan. 25, 2018, 9 pages.

Berni et al., "Mapping Canopy Conductance and CWSI in Olive Orchards Using High Resolution Thermal Remote Sensing Imagery", in: Remote Sensing Environment 113 [online], Jun. 28, 2009 [retrieved on Jan. 4, 2018], Retrieved from the Internet: <URL:https://www.sciencedirect.com/science/article/pii/S0034425709002090>, pp. 2380-2388.

Smith, Adam Brook, "Soil Moisture Monitoring with Ground-Based Gravity Data," Dissertation University of Melbourne, Department of Infrastructure Engineers, 2013, 397 pages.

* cited by examiner

MULTI-DEPTH SOIL MOISTURE MONITORING SYSTEMS AND METHODS TO EVALUATE SOIL TYPE, PACKAGED IN SMALL ROUND POLYVINYL CHLORIDE TUBE, WITH POTTING AND RODENT PROTECTION, FOR EFFECTIVE MEASUREMENTS AND INSTALLATION

CROSS REFERENCE TO RELATED APPLICATIONS

This non-provisional patent application claims the benefit and priority of U.S. Provisional Application Ser. No. 62/434,340 filed on Dec. 14, 2016, which is hereby incorporated by reference herein in its entirety including all references and appendices cited therein.

FIELD OF THE TECHNOLOGY

The present technology relates generally to farm irrigation, and more specifically, but not by limitation, to systems and methods for improving irrigation for various plants, trees, and other flora in a farm in order to improve farm performance.

SUMMARY OF THE PRESENT TECHNOLOGY

According to some exemplary embodiments, the present disclosure is related in general to a soil moisture monitoring system comprising a first PVC pipe holding one or more sensing units, a top of the first PVC pipe mated to a "T" intersection, and a base of the "T" intersection mated to a rodent resistant cord. The first PVC pipe is generally round in shape with one or more flat surfaces of approximately six inches in length, each flat surface at an approximately 90 degree angle relative to a next closest flat surface. Each of the one or more sensing units further comprises a controller communicatively coupled between two antennas. Each of the one or more sensing units may further comprise a programming port in close proximity to the controller. The controller on each of the one or more sensing units may be configured to be independently programmable with its own unique program. In most exemplary embodiments, four sensing units (although this number is not limited) may be vertically stacked on the first PVC pipe and configured to transmit eight separate directional radio frequencies into nearby dirt, each of the eight separate directional radio frequencies vertically spaced six inches apart.

Each antenna may further comprise two traces nearly on top of each other. The two traces may be configured to cause opposing magnetic forces against each other, and the two traces may be configured in a serpentine form. Each antenna is on a separate printed circuit board with each trace configured to receive an alternating current ("AC") wave. Each of the two traces are generally separated by an approximately 5 millimeter thick FR-4 fiberglass core, and each of the two traces may be copper plated with gold on either side of the approximately 5 millimeter thick FR-4 fiberglass core. Moreover, the AC wave is of the same frequency that matches only to each of the traces. The AC waveform is created by a low power oscillator that is powered by a battery. In turn, the antenna induces a directional radio frequency wave into nearby dirt of about 18 inches of radius. The directional radio frequency wave may then cause resonance in the conductor.

In most exemplary embodiments, a pressure relief vent within the "T" intersection is configured to run vertically with the first PVC pipe. Each of the sensing units may be connected to four wires running an interior length of the first PVC pipe to the "T" intersection and through the base of the "T" intersection and through the rodent resistant cord. The four wires may be ground, power, data and data bar. A second PVC pipe may encase and seal the first PVC pipe.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

According to some embodiments, the present disclosure provides solutions to increase farm efficiency and profitability by reducing water, pesticide, and other resource consumption and increasing yield.

Figure 1:
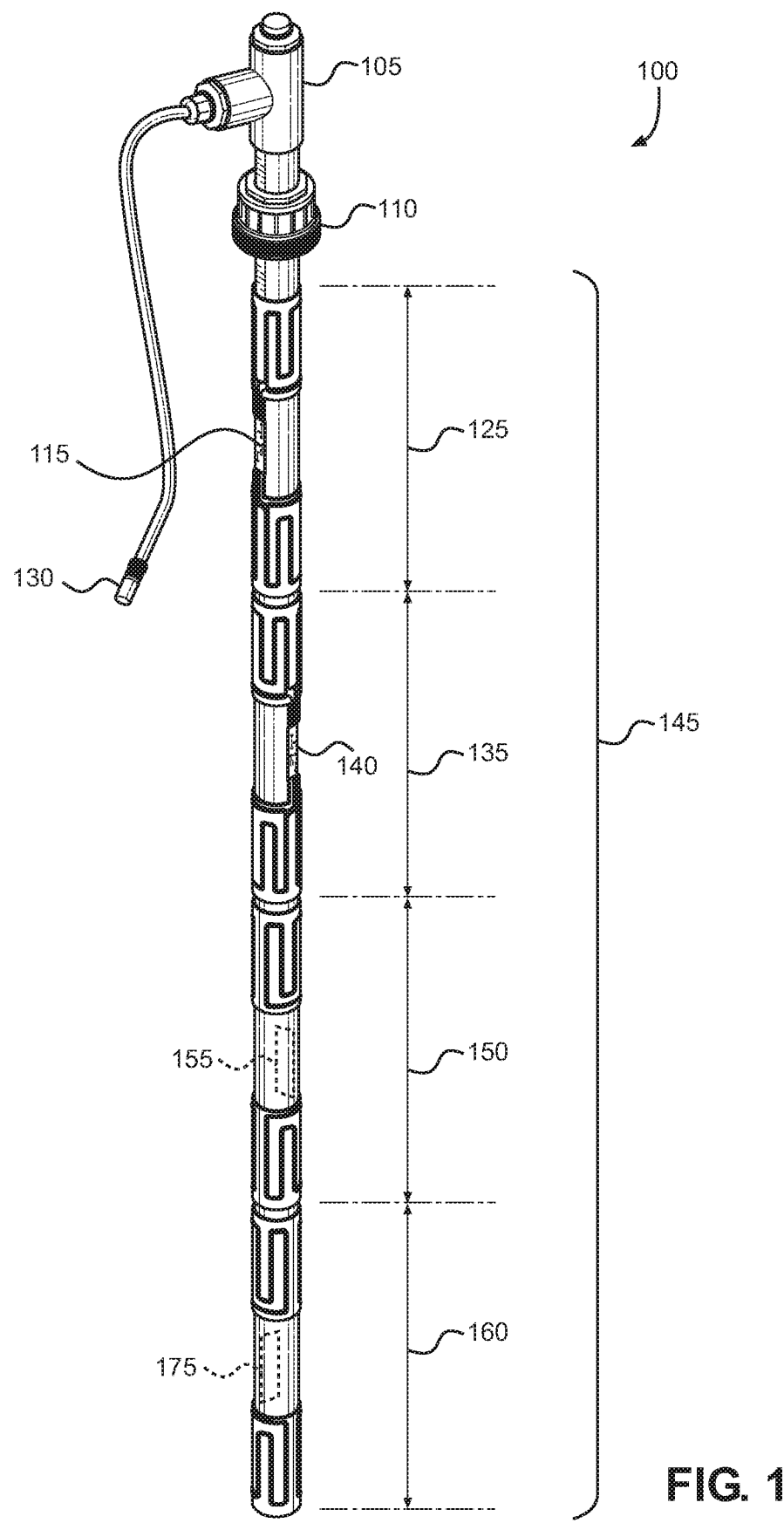
FIG. 1 shows an exemplary soil moisture monitoring system for practicing aspects of the present disclosure.

FIG. 1 shows an exemplary soil moisture monitoring system for practicing aspects of the present disclosure.

Shown in FIG. 1 as part of the exemplary soil moisture monitoring system 100 are "T" intersection 105, threaded connector 110, controllers 115, 140, 155 and 175, sensing units 125, 135, 150 and 160, rodent resistant cord 130 and first PVC pipe 145.

According to various exemplary embodiments, a soil moisture monitoring system 100 comprises a first PVC pipe 145 holding one or more sensing units 125, 135, 150 and/or 160, a top of the first PVC pipe 145 mated to a "T" intersection 105 and a base of the "T" intersection 105 mated to a rodent resistant cord 130. In numerous exemplary embodiments, the first PVC pipe 145 is Schedule 80 in thickness, one-half inch in diameter and generally round in shape with one or more flat surfaces of approximately six inches in length, each flat surface at an approximately 90 degree angle relative to a next closest flat surface. Advantageously, the approximately 90 degree angles interspersed one by one across the pipe for the controllers enhance the structural integrity of the pipe.

In many embodiments, the "T" intersection 105 functions as a moisture relief valve so that any moisture accumulated in the pipe can vent out. In some cases, this may be a Donaldson vent.

In most exemplary embodiments, each sensing unit is approximately a foot in length, each having an independent computer.

Figure 2:
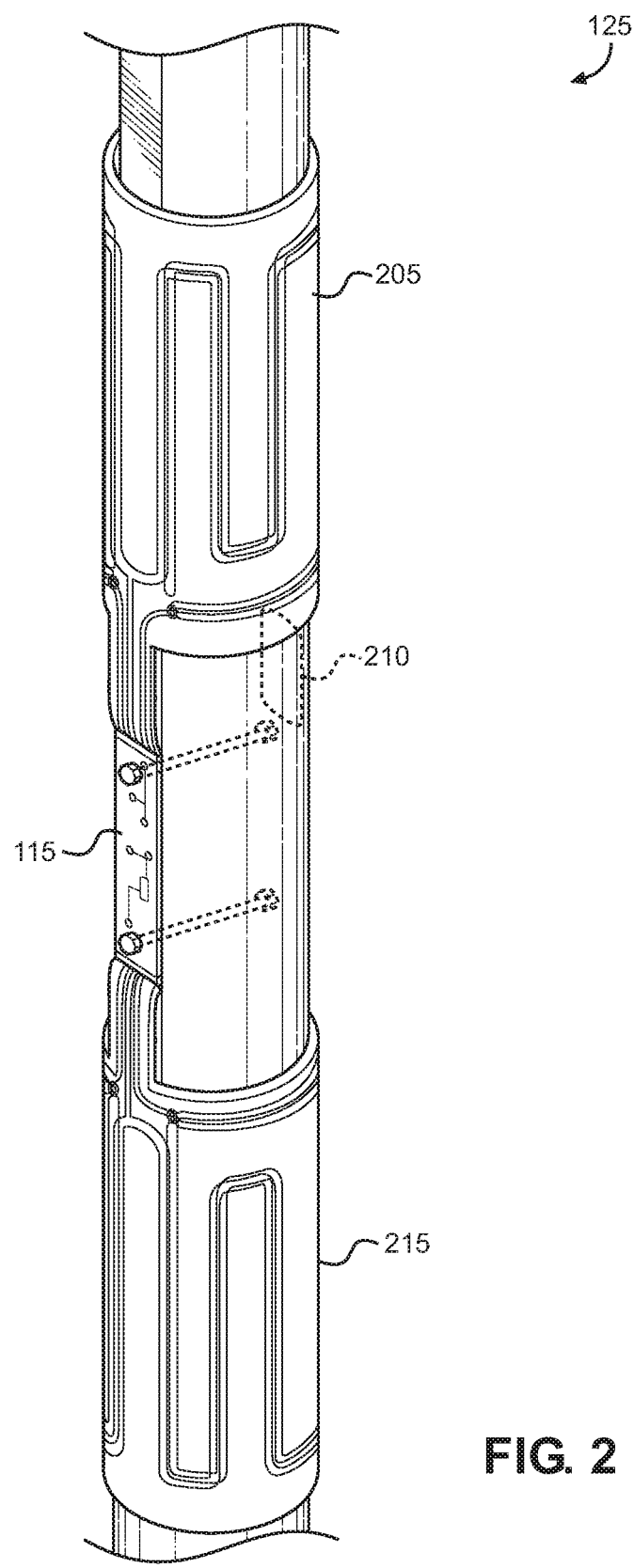
FIG. 2 shows an exemplary sensing unit for practicing aspects of the present disclosure.

FIG. 2 shows an exemplary sensing unit for practicing aspects of the present disclosure.

Shown in FIG. 2 as part of the exemplary sensing unit 125 (FIG. 1) are antennas 205 and 215, controller 115 (FIG. 1), and programming port 210.

In most exemplary embodiments, each of the one or more sensing units (such as sensing unit 125) further comprise a controller (such as controller 115) communicatively coupled between two antennas (such as antennas 205 and 215). In some exemplary embodiments, the antennas may be mounted on tape wrapped around the first PVC pipe 145. In many exemplary embodiments, the controller is connected by screws on a flat surface as described herein. Additionally, each of the one or more sensing units further comprises a programming port (such as programming port 210) in close proximity to the controller (such as controller 115). In some exemplary embodiments, a Flash program such as PICkit 3 may be used to program the controllers.

Furthermore, the controller on each of the one or more sensing units may be configured to be independently programmable with its own unique program. Four sensing units may be vertically stacked on the first PVC pipe and configured to transmit eight separate directional radio frequencies into nearby dirt, each of the eight separate directional radio frequencies vertically spaced six inches apart.

Figure 3:
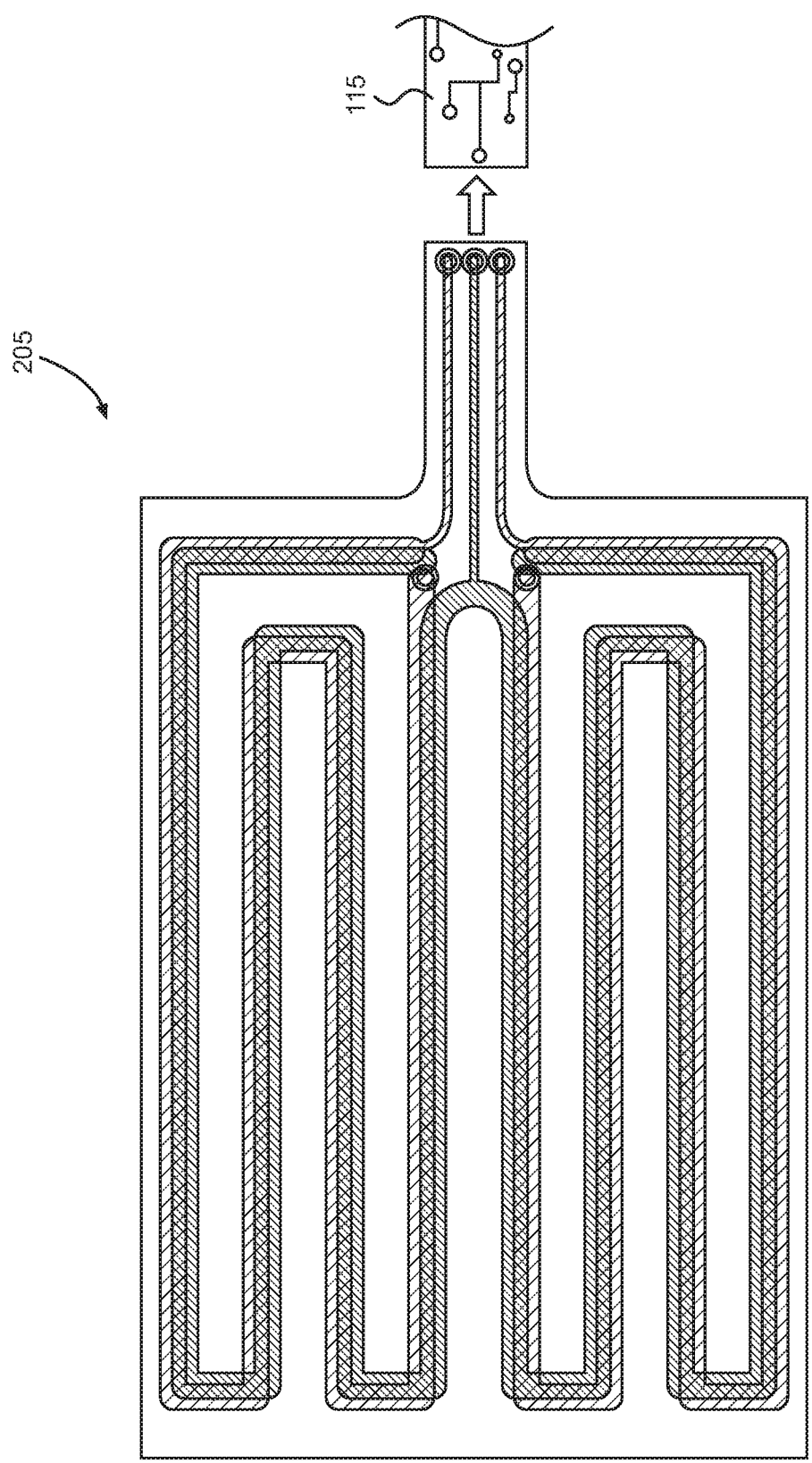
FIG. 3 shows an exemplary antenna for practicing aspects of the present disclosure.

FIG. 3 shows an exemplary antenna for practicing aspects of the present disclosure.

Shown in FIG. 3 as part of the exemplary antenna 205 (FIG. 2) is the connection of antenna 205 to exemplary controller 115 (FIG. 1).

In various exemplary embodiments, each antenna further comprises two traces nearly on top of each other and the two traces are configured to cause opposing magnetic forces against each other. Additionally, the two traces are configured in a serpentine form. Each antenna may be configured on a separate printed circuit board with each trace configured to receive an alternating current ("AC") wave. In general, each of the two traces are separated by an approximately 5 millimeter thick FR-4 fiberglass core. Each of the two traces may be copper plated with gold on either side of the approximately 5 millimeter thick FR-4 fiberglass core.

In further exemplary embodiments, the AC wave is of the same frequency that matches only to each of the traces. The AC waveform is created by a low power oscillator that is powered by a battery. The antenna induces a directional radio frequency wave into nearby dirt of about 18 inches of radius. The directional radio frequency wave causes resonance in the conductor.

Advantageously, with this configuration, there is less than a one percent variance and each sensing unit can measure a larger volume of influence, inducing a wave into the dirt of about a foot or 18 inches of radius. In contrast to a device that induces a wave into the dirt of about a four inch radius, with the present exemplary embodiments, foreign objects that are in the field of influence do not have as big of an influence when measuring a larger volume of dirt.

Figure 4:
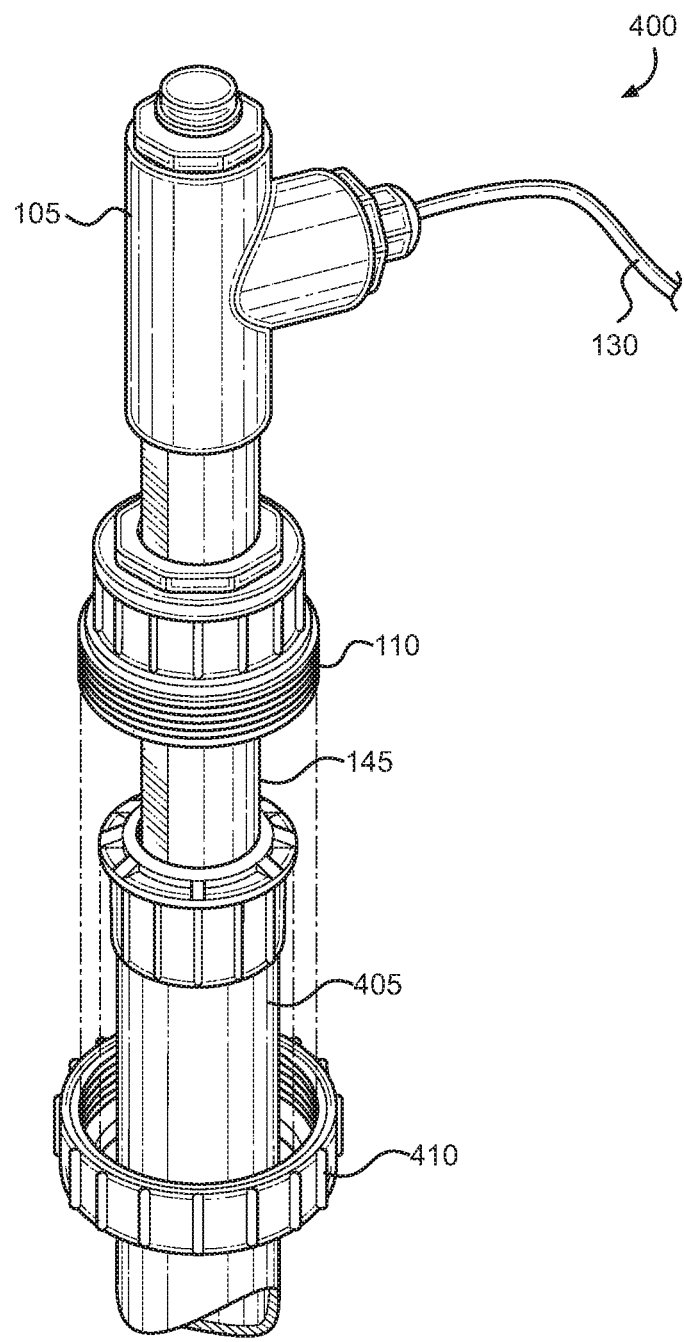
FIG. 4 shows an exemplary upper assembly for practicing aspects of the present disclosure.

FIG. 4 shows an exemplary upper assembly for practicing aspects of the present disclosure.

Shown in FIG. 4 as part of the exemplary upper assembly 400 is "T" intersection 105 (FIG. 1), rodent resistant cord 130 (FIG. 1), threaded connector 110 (FIG. 1), first PVC pipe 145 (FIG. 1), second PVC pipe 405 and connecting ring 410.

According to many exemplary embodiments, a pressure relief vent within the "T" intersection is configured to run vertically with the first PVC pipe. Also within the "T" intersection 105 is a RS-485 serial interface, which is a differential serial standard protocol that is connected to sensing units 125, 135, 150 and 160 (FIG. 1). With power and a serial bus going down the middle of the PVC pipe, it is a full-on interface. At 9600 baud, in further exemplary embodiments, up to two thousand sensing units may be installed on a PVC pipe to monitor a two thousand foot deep hole in the ground.

Figure 5:
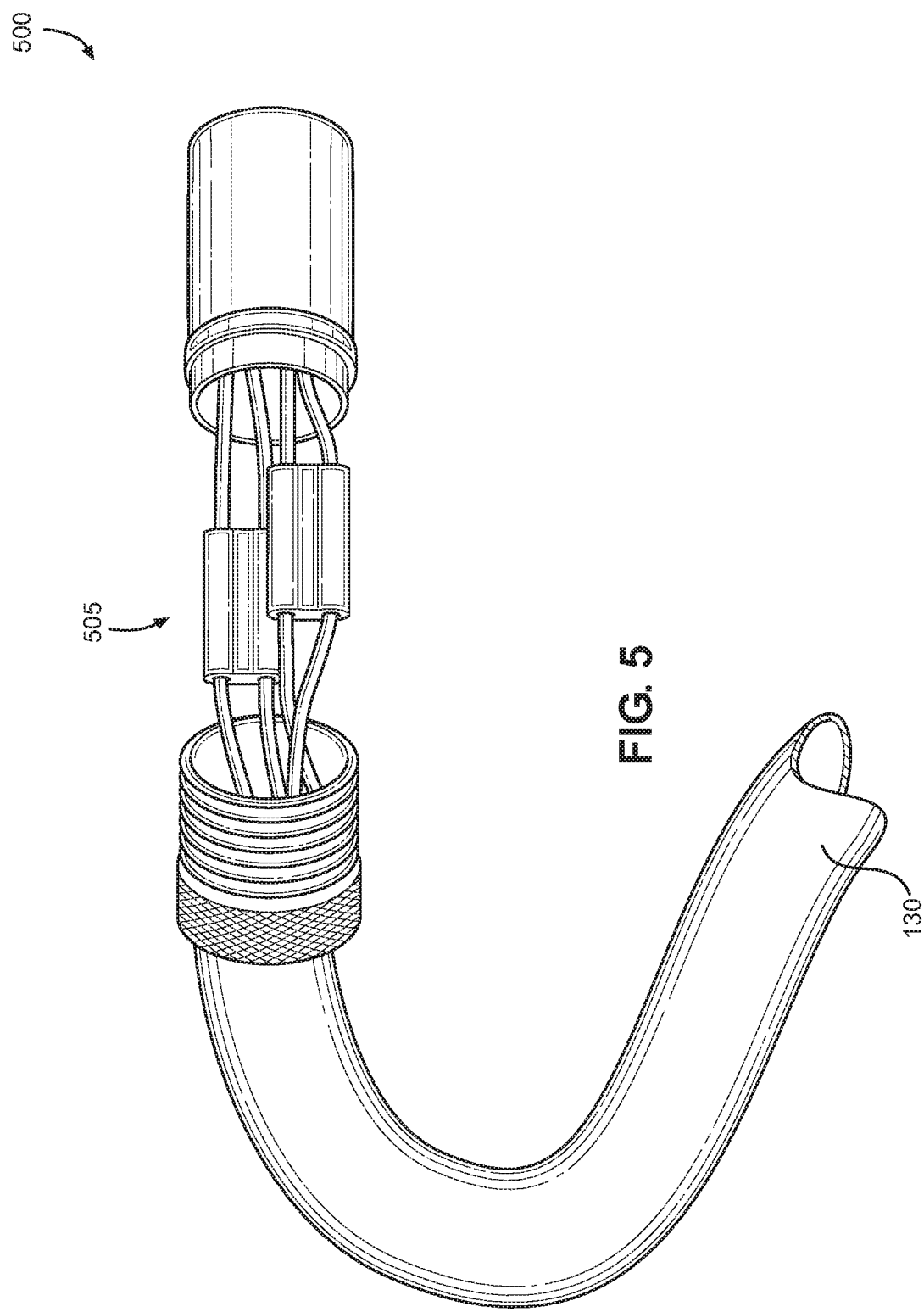
FIG. 5 shows an exemplary rodent resistant cord with wiring from the exemplary soil moisture monitoring system for practicing aspects of the present disclosure.

FIG. 5 shows an exemplary rodent resistant cord with wiring from the exemplary soil moisture monitoring system for practicing aspects of the present disclosure.

Shown in FIG. 5 as part of the exemplary rodent resistant cord with wiring from the exemplary soil moisture monitoring system 500 is four wires 505 and rodent resistant cord 130. In general, the rodent resistant cord exits the "T" intersection 105 (FIG. 1) at a vertical angle.

In various exemplary embodiments, each of the sensing units are connected to four wires running an interior length of the first PVC pipe 145 (FIG. 1) to the "T" intersection 105 and through the base of the "T" intersection 105 and through the rodent resistant cord 130. The four wires 505 are ground, power, data and data bar.

Figure 6:
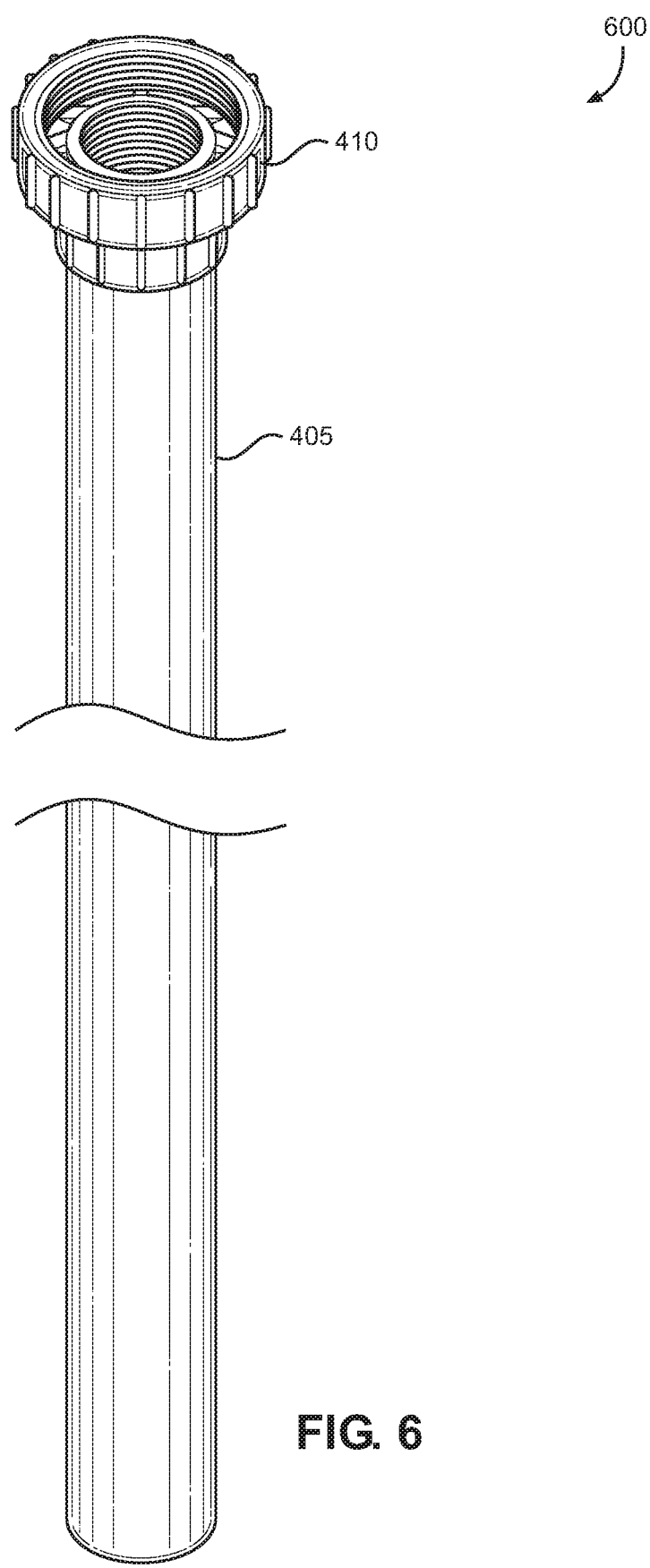
FIG. 6 shows an exemplary encasement assembly for encasing the exemplary soil moisture monitoring system for practicing aspects of the present disclosure.

FIG. 6 shows an exemplary encasement assembly for encasing the exemplary soil moisture monitoring system for practicing aspects of the present disclosure.

Shown in FIG. 6 as part of the exemplary encasement assembly 600 for encasing the exemplary soil moisture monitoring system 100 (FIG. 1) is connecting ring 410 (FIG. 4) and second PVC pipe 405 (FIG. 4).

In various exemplary embodiments, the second PVC pipe 405 encases and seals the first PVC pipe 145 (FIG. 1). Advantageously, the resulting configuration allows for the easy removal of the inner first PVC pipe 145 for maintenance and programming of the controllers. Upon installation of the fully encapsulated unit vertically into the ground (in some cases with a Concord drill bit), ground level is approximately where connecting ring 410 sits flush on the ground while encompassing threaded connector 110 (FIG. 1), while forming a waterproof seal. Such a set-up allows for easy and consistent installations of numerous units. Accordingly, at this point, the center of the vertical-most antenna of sensing unit 125 (FIG. 1) is approximately 3 inches from the top of the ground. Thus readings may be taken every six inches.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. Exemplary embodiments were chosen and described in order to best explain the principles of the present disclosure and its practical application, and to enable others of ordinary skill in the art to understand the present disclosure for various embodiments with various modifications as are suited to the particular use contemplated.

Aspects of the present disclosure are described above with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While this technology is susceptible of embodiment in many different forms, there is shown in the drawings and will herein be described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be limiting of the technology. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that like or analogous elements and/or components, referred to herein, may be identified throughout the drawings with like reference characters. It will be further understood that several of the figures are merely schematic representations of the present disclosure. As such, some of the components may have been distorted from their actual scale for pictorial clarity.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the following description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

It is noted at the outset that the terms "coupled," "connected", "connecting," "electrically connected," etc., are used interchangeably herein to generally refer to the condition of being electrically/electronically connected. Similarly, a first entity is considered to be in "communication" with a second entity (or entities) when the first entity electrically sends and/or receives (whether through wireline or wireless means) information signals (whether containing data information or non-data/control information) to the second entity regardless of the type (analog or digital) of those signals. It is further noted that various figures (including component diagrams) shown and discussed herein are for illustrative purpose only, and are not drawn to scale.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel, or may be performed at different times.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Furthermore, relative terms such as "below," "lower," "above," and "upper" may be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings is turned over, then the elements described as being on the "lower" side of other elements would then be oriented on "upper" sides of the other elements. Similarly, if the device in one of the figures is turned over, elements described as "below" or "beneath" other elements would then be oriented "above" the other elements. Therefore, the example terms "below" and "lower" can, therefore, encompass both an orientation of above and below.

While various embodiments have been described above, it should be understood that they have been presented by way of example only, and not limitation. The descriptions are not intended to limit the scope of the invention to the particular forms set forth herein. To the contrary, the present descriptions are intended to cover such alternatives, modifications, and equivalents as may be included within the spirit and scope of the invention as defined by the appended claims and otherwise appreciated by one of ordinary skill in the art. Thus, the breadth and scope of a preferred embodiment should not be limited by any of the above-described exemplary embodiments.

What is claimed is:

1. A soil moisture monitoring system comprising:
   a first PVC pipe holding one or more sensing units;
   a top of the first PVC pipe mated to a "T" intersection; and
   a base of the "T" intersection mated to a rodent resistant cord.

2. The soil moisture monitoring system of claim 1, further comprising:
   the first PVC pipe being generally round in shape with one or more flat surfaces of approximately six inches in length, each flat surface at an approximately 90 degree angle relative to a next closest flat surface.

3. The soil moisture monitoring system of claim 1, each of the one or more sensing units further comprising a controller communicatively coupled between two antennas.

4. The soil moisture monitoring system of claim 3, each of the one or more sensing units further comprising a programming port in close proximity to the controller.

5. The soil moisture monitoring system of claim 4, the controller on each of the one or more sensing units configured to be independently programmable with its own unique program.

6. The soil moisture monitoring system of claim 5, further comprising vertically stacking four sensing units on the first PVC pipe configured to transmit eight separate directional radio frequencies into nearby dirt, each of the eight separate directional radio frequencies vertically spaced six inches apart.

7. The soil moisture monitoring system of claim 6, each antenna further comprising two traces nearly on top of each other.

8. The soil moisture monitoring system of claim 7, the two traces configured to cause opposing magnetic forces against each other.

9. The soil moisture monitoring system of claim 8, the two traces configured in a serpentine form.

10. The soil moisture monitoring system of claim 9, each antenna on a separate printed circuit board with each trace configured to receive an alternating current ("AC") wave.

11. The soil moisture monitoring system of claim 10, each of the two traces separated by an approximately 5 millimeter thick FR-4 fiberglass core.

12. The soil moisture monitoring system of claim 11, each of the two traces copper plated with gold on either side of the approximately 5 millimeter thick FR-4 fiberglass core.

13. The soil moisture monitoring system of claim 12, wherein the AC wave is of a same frequency that matches only to each of the traces.

14. The soil moisture monitoring system of claim 13, wherein the AC wave is created by a low power oscillator that is powered by a battery.

15. The soil moisture monitoring system of claim 14, wherein each antenna induces a directional radio frequency wave into nearby dirt of about 18 inches of radius.

16. The soil moisture monitoring system of claim 15, further comprising:
the directional radio frequency wave causing resonance in a conductor.

17. The soil moisture monitoring system of claim 1, further comprising:
a pressure relief vent within the "T" intersection configured to run vertically with the first PVC pipe.

18. The soil moisture monitoring system of claim 17, further comprising each of the sensing units being connected to four wires running an interior length of the first PVC pipe to the "T" intersection and through the base of the "T" intersection and through the rodent resistant cord.

19. The soil moisture monitoring system of claim 18, wherein the four wires are ground, power, data and data bar.

20. The soil moisture monitoring system of claim 1, further comprising:
a second PVC pipe encasing and sealing the first PVC pipe.

* * * * *